United States Patent
Egea Bermejo et al.

(10) Patent No.: US 8,939,017 B2
(45) Date of Patent: Jan. 27, 2015

(54) SURFACE-DEPOSITED PARTICLE AND SUBSTANCE SAMPLING, DILUTION AND ANALYSIS DEVICE

(75) Inventors: Eduardo Egea Bermejo, Barranquilla (CO); Marco Sanjuan Mejia, Barranquilla (CO)

(73) Assignee: Fundacion Universidad del Norte, Barranquilla (CO)

( * ) Notice: Subject to any disclaimer, the term of this patent is extended or adjusted under 35 U.S.C. 154(b) by 391 days.

(21) Appl. No.: 13/318,082

(22) PCT Filed: Jan. 30, 2010

(86) PCT No.: PCT/IB2010/000176
§ 371 (c)(1),
(2), (4) Date: Mar. 14, 2012

(87) PCT Pub. No.: WO2010/086730
PCT Pub. Date: Aug. 5, 2010

(65) Prior Publication Data
US 2012/0160016 A1    Jun. 28, 2012

(30) Foreign Application Priority Data
Jan. 30, 2009    (CO) .................................. 09008859

(51) Int. Cl.
| | |
|---|---|
| G01N 11/00 | (2006.01) |
| G01N 1/04 | (2006.01) |
| B01L 3/00 | (2006.01) |
| G01N 1/38 | (2006.01) |

(52) U.S. Cl.
CPC ................ *G01N 1/04* (2013.01); *B01L 3/5023* (2013.01); *G01N 1/38* (2013.01); *B01L 3/502* (2013.01); *B01L 2200/082* (2013.01); *B01L 2200/10* (2013.01); *B01L 2200/16* (2013.01); *B01L 2300/0841* (2013.01)
USPC ........................................ 73/53.01; 73/864.71

(58) Field of Classification Search
USPC .................................. 73/53.01, 61.59, 864.71
See application file for complete search history.

(56) References Cited

U.S. PATENT DOCUMENTS

| | | | |
|---|---|---|---|
| 6,375,896 B1 | 4/2002 | Wuske et al. | |
| 2004/0180451 A1 | 9/2004 | Cooke et al. | |

(Continued)

FOREIGN PATENT DOCUMENTS

| | | |
|---|---|---|
| DE | 19909891 C1 | 1/2001 |
| GB | 2378753 A | 2/2003 |

(Continued)

OTHER PUBLICATIONS

PCT International Search Report for International Application No. PCT/IB2010/000176, mailed May 31, 2010.

*Primary Examiner* — Hezron E Williams
*Assistant Examiner* — David Z Huang
(74) *Attorney, Agent, or Firm* — Holland & Hart LLP

(57) ABSTRACT

A device for sampling, diluting and analyzing particles and substances normally located on surfaces. The device includes a collection system which, through a rotating collecting surface and a scraper gathers the sample. The device also includes a tank-like storage system to store the diluting solution and a dilution chamber that permits the sample to mix with the solution and be diluted. This mixture is subsequently placed in contact with a detection system which is capable of discerning the presence or not of the substance being sampled.

16 Claims, 13 Drawing Sheets

(56) References Cited

U.S. PATENT DOCUMENTS

2004/0187610 A1* 9/2004 Kawano et al. ............ 73/864.01
2008/0003564 A1* 1/2008 Chen et al. ........................ 435/5

FOREIGN PATENT DOCUMENTS

| WO | 0111374 A2 | 2/2001 |
| WO | 2007100500 A2 | 9/2007 |

* cited by examiner

SURFACE-DEPOSITED PARTICLE AND SUBSTANCE SAMPLING, DILUTION AND ANALYSIS DEVICE

FIELD OF THE INVENTION

Surface-deposited substance and particle sample collection and its latter analysis through dilution and reaction is of interest in the chemical, pharmaceutical, health, security, and criminology sectors, amongst others.

The prior art contemplates several attempts to provide surface particle and substance sampling. However, these devices comprise two or more units, require liquid or solid handling or dispensing, or the collection of very small substance or particle quantities rubbing a small, fixed and saturable surface against the surface containing the matter of interest.

Referring to FIG. 1A, document US2004180451 discloses a diagnostic testing device for collecting and testing substances comprising a housing (100), a filter (101) configured to capture substances entrained in an air flow (102) and a reservoir (103) for storing and evaluating the substances captured on the filter (101). The collecting mechanism of this invention requires air flow (102) which implies additional powered devices in order to collect substances. The air flow (102) may let undesirable particles to flow within the device and affect the results of the analysis. Additionally, this invention retains the measured particles directly on the filter, preventing the device providing the possibility of a prior dilution.

As shown in FIG. 1B, document DE19909891 discloses an immunoassay device comprising a housing (150) with an elevated portion having a central opening (151) containing a swab stick for sampling and reaction zone (152) with signal zones in capillary communication with the swab stick and a window in the housing above the reaction zone (152). This device does not provide the possibility of a prior dilution and also saturates the sampling surface with the substance of interest. This may increase the possibility of erroneous readings.

SUMMARY OF THE INVENTION

The invention generally comprises a device that allows for the collection of surface-deposited substance or particle samples, storage thereof, dilution of said substances in solution or test liquid, and analysis thereof in an analysis chamber. This device operates as a self-contained unit requiring no direct handling of the material to be analyzed of the dilution agent. This device allows for the prior verification of the amount of particles or material to be analyzed.

The device uses a rotational collection surface, which allows for repetitive substance or particle collection and separation in a manner that the amount of material to be collected is limited by the storage capacity, not by the collecting capacity.

This device also allows for the use of a controlled amount of liquid for dilution and does not generate waste containers. The amount of liquid stored in the container is determined as a function of the detection concentration threshold for the specific product to be analyzed. In a preferred embodiment, once the sampling unit or units, comprising the device, have been used, it is discarded as a whole. Another advantage of the device is it is self-contained. It does not require any accessories nor additional units (such as vacuums or the like).

DETAILED DESCRIPTION OF THE INVENTION

The present invention is a device generally comprising four parts corresponding to: i) a collection system for sample collection; ii) a storage system containing the necessary fluid (s) for dilution or reaction of the sample; iii) a dilution chamber; and iv) a detection system for sample reception and analysis.

Figure 1A:
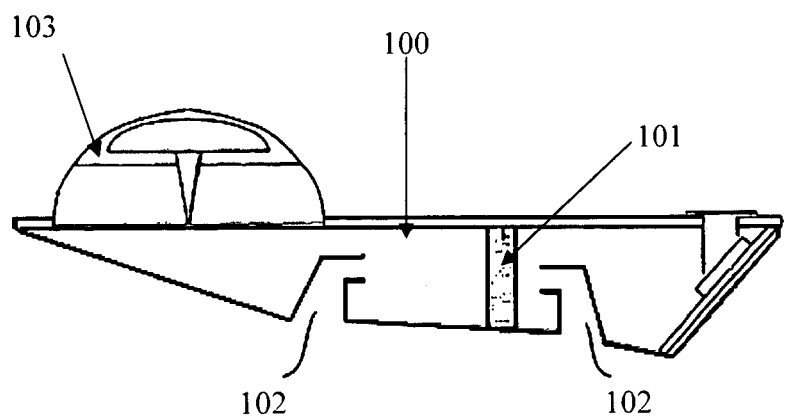
FIG. 1A is a lateral view of a device described in US2004180451.
Figure 1B:
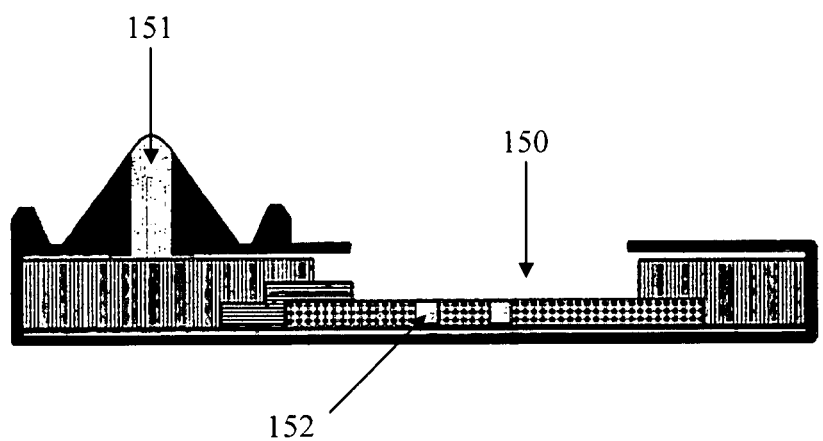
FIG. 1B is a lateral view of a device described in DE19909891.
Figure 2A:
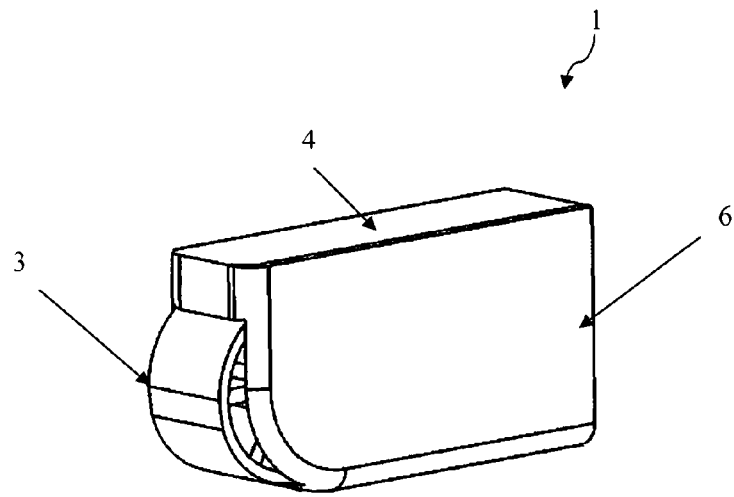
FIG. 2A is an isometric view of a preferred embodiment of the claimed device.
Figure 2B:
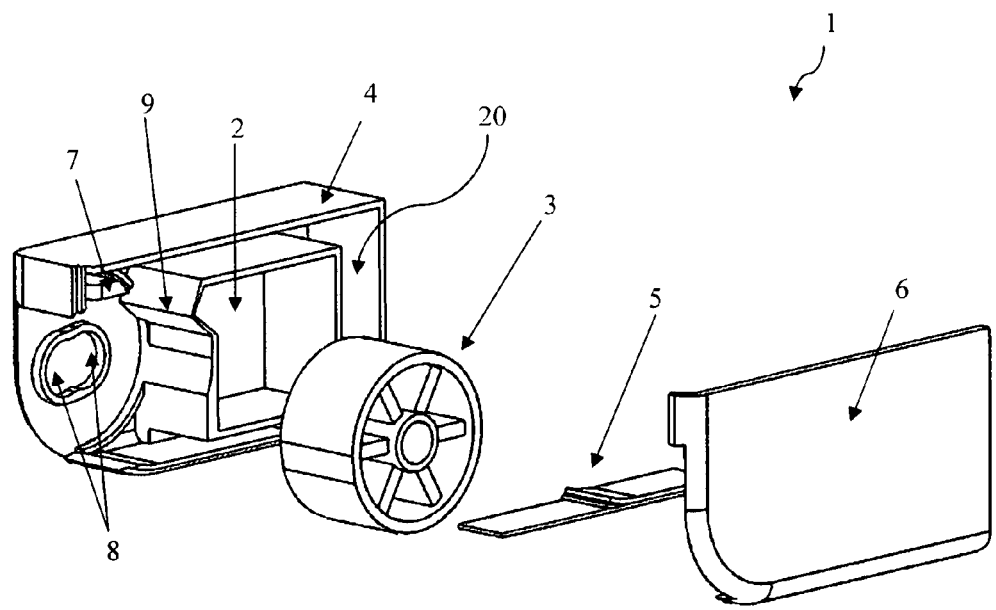
FIG. 2B shows an exploded isometric view of a preferred embodiment of the claimed device.
Figure 3:
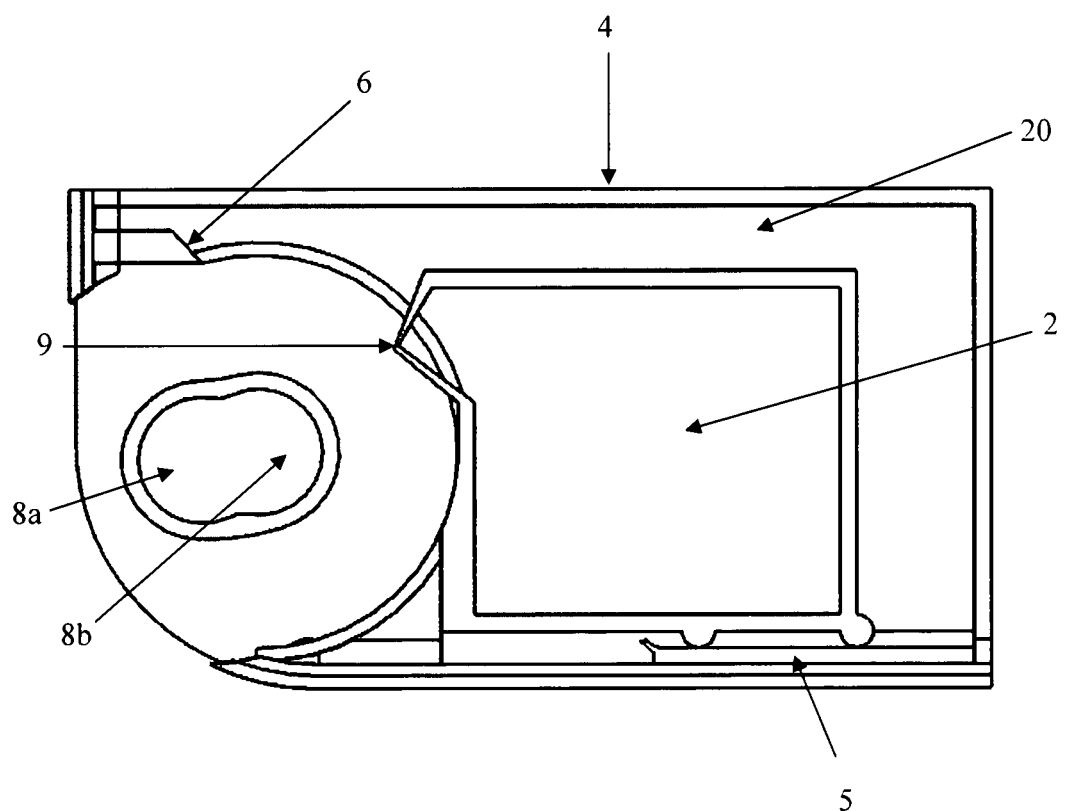
FIG. 3 shows a lateral internal view of a preferred embodiment of the claimed device.

Referring to FIGS. 2A, 2B and 3, there is shown a first embodiment wherein the device (1) includes:
i) a storage tank (2);
ii) a roll (3);
iii) a cover base (4);
iv) a dilution chamber (20);
v) a membrane (5);
vi) a cap (6);
vii) a track (8); and
viii) a scraper (7).

The storage tank (2) contains the fluid(s) for dilution or reaction of the sample and comprises a breakable protrusion (9).

Dilution chamber (20) is a closed volume defined by the internal walls of device (1), roll (3) in the sample preparation position, scraper (7) and membrane (5).

The cap (6) serves as support for the membrane (5) and as a seal for the solution contained in the storage tank (2). The material, both of the cover base (4) and cap (6), is preferably a polymer due to its low cost and convenience provided when manufacturing using molds. In preferred embodiments, the polymer of the device-s structure is partially translucent in order to let the user observe the volume of the collected sample, the sample's dilution liquid and the detection results.

Figure 4A:
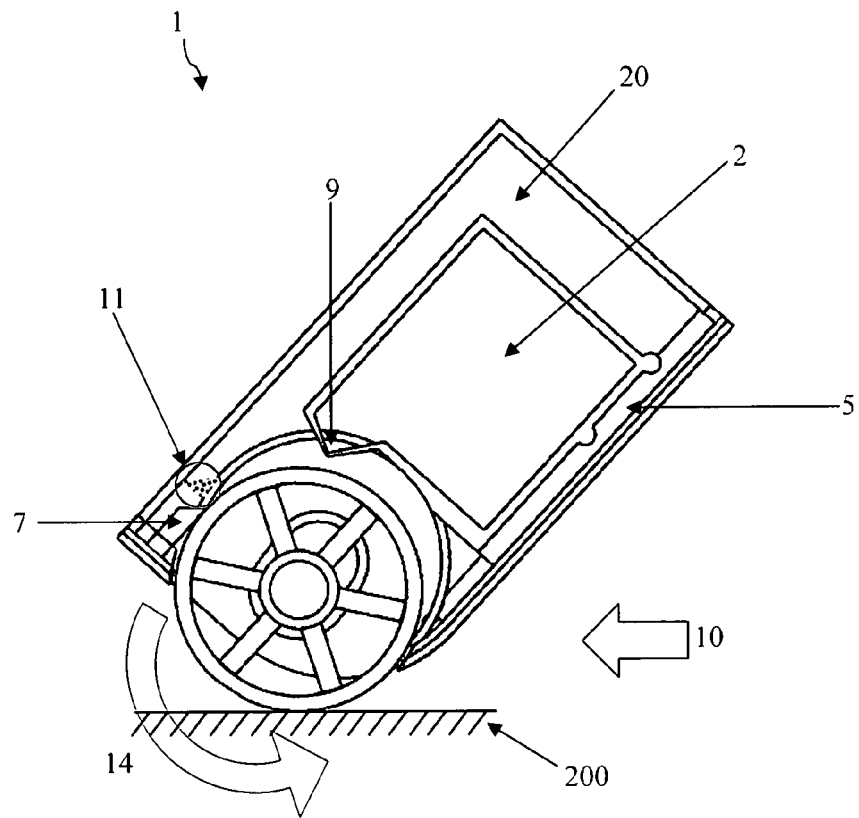
FIG. 4A shows the configuration of the device in FIG. 3 at the moment of collection.
Figure 4B:
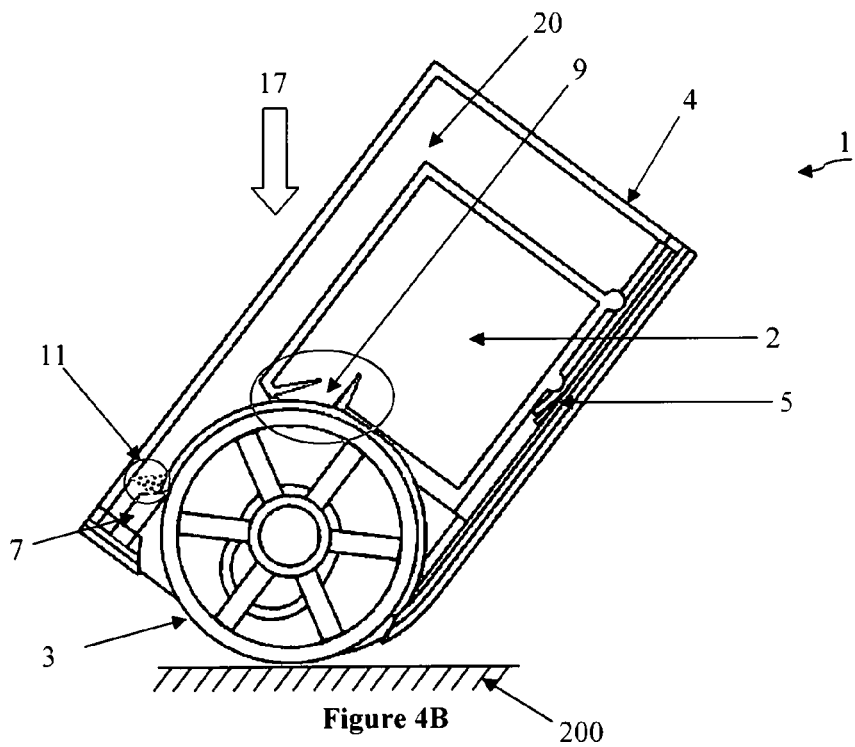
FIG. 4B shows the configuration of the device in FIG. 3 at the moment of dilution and analysis.

Referring to FIGS. 3, 4A and 4B, roll (3) is made of a rough material working as an adhesive such that when rotating the roll (3) over the sample surface, the particulates adheres to the surface of the roll (3). The material of the roll surface allows the particulates to be adhered to the roll (3) while device (1) is moved over the sample surface. The roll surface material should also let the sampled particles to be removed easily when making contact with the scraper (7). A preferred material is Ethyl Vinyl Acetate. A preferred porosity of roll material is 15 µm, although this will necessarily vary with the type of substance being sampled.

Cover base (4) has a track (8) (cap (6) also has an equivalent counterpart track on its inside surface) that guides the axis of roll (3) from the first position (8a) (when the device (1) is sampling) to the second position (8b) (when the device (1) proceeds with the sample preparation). Roll (3) can be located in one of these positions.

The following is the method of use of the first embodiment (1):

Step 1: Sample Collection

Referring to FIG. 4A, device (1) is placed on the sample surface (200) and the roll (3) is rotated by a forward motion (10) and rolls in counterclockwise direction (14). Sample (11) is collected by roll (3) along its rough surface as it rolls and is removed by scraper (7). The forward motion (10) will continue in this fashion over the zone needing analysis until the required sample quantity is obtained in order to achieve detection (the sample amount can be measured using a volume indicator visible through a transparent cap (6)). The sample collected (11) is stored between the scraper (7) and the device's wall as shown in FIG. 4B.

Step 2: Sample Preparation

Referring to FIG. 4B, after obtaining the needed amount for the corresponding detection reading, a force (17) is applied on the device (1) when it is still on the surface where the sample is collected. This displaces roll (3) along track (8) from, referring to FIG. 3, position (8a) to position (8b). When this displacement occurs, and because tank (2) comprises a protrusion (9) into the zone where roll (3) arrives at its final position (8b), and said protrusion (9) is weakened by a lesser thickness together with a layout prone for concentrating stresses, tank (2) breaks at or around protrusion (9).

When protrusion (9) of tank (2) is broken, roll (3) seals dilution chamber (20). At the same time, the solvent exits the tank (2) and floods the collected sample (11). The dilution chamber (20) works as a cavity for housing the dilution liquid together with the collected sample.

Subsequently, device (1) is separated from the surface, and keeping the same inclination with respect to the surface, it is shaken in order to achieve a substantially homogenous solution inside the dilution chamber (20).

Step 3: Sample Analysis

Figure 5A:
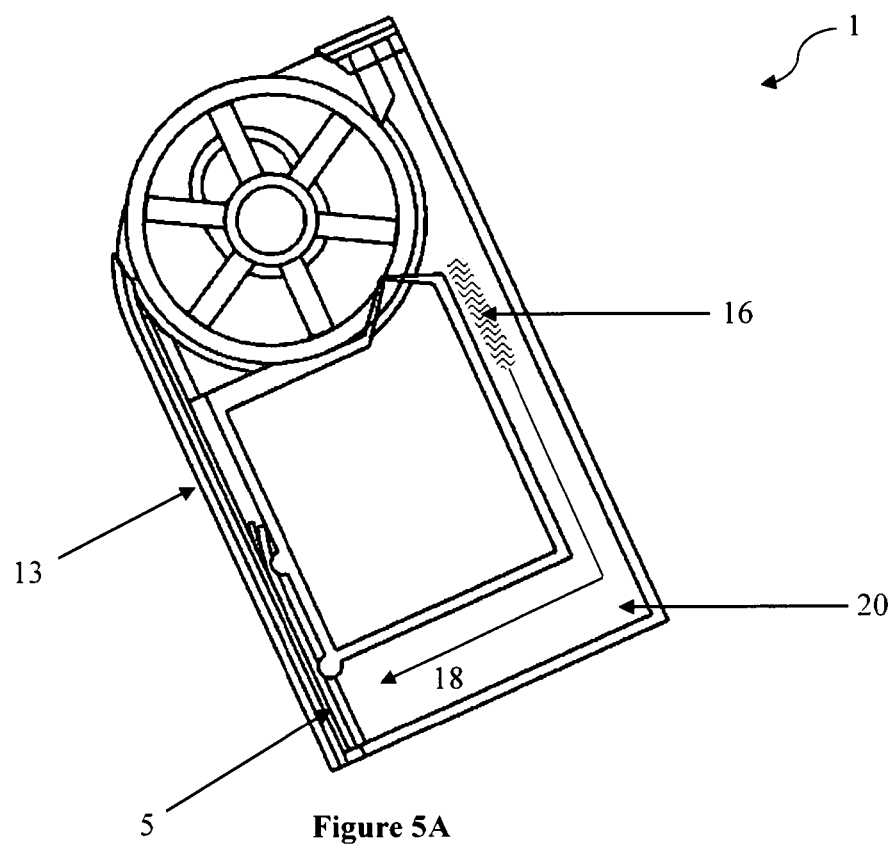
FIG. 5A shows the transport path of the solution in the device of FIG. 3.
Figure 5B:
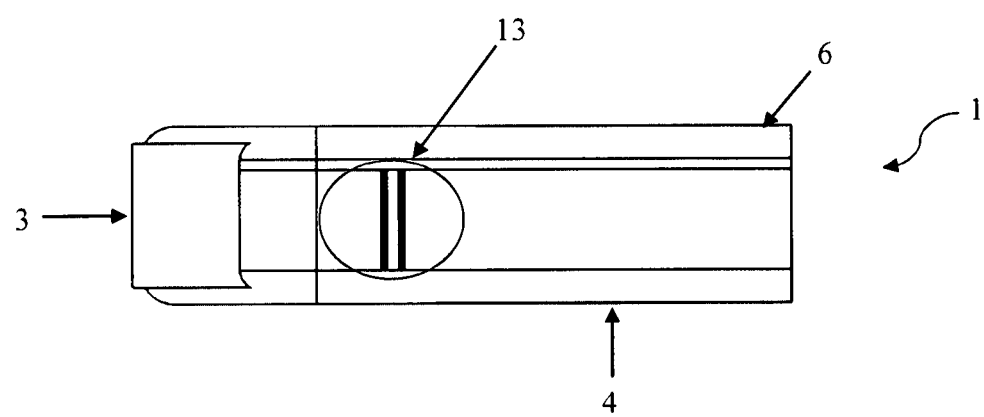
FIG. 5B shows an inferior view of the device of FIG. 3 displaying the result reading mechanism.

After shaking the sample and homogenizing it, device (1) is rotated until reaching the position shown in FIG. 5A; this way, the solution (16) is directed towards the membrane (5) along path (18). Through the membrane (5), part of the solution is absorbed, this way reacting with the components fixed therein and providing the desired dilution results. The results (13) are shown in the bottom side of the device (1) as shown in FIG. 5B. Membrane (5) is obviously designed to secure the required detection for the type of material being sampled. For example, if the purpose is detecting a specific kind of mite protein, the membrane (5) should contain a solution that reacts when that kind of mite protein is present in the dilution, showing the results on one side of the membrane (5).

Figure 6:
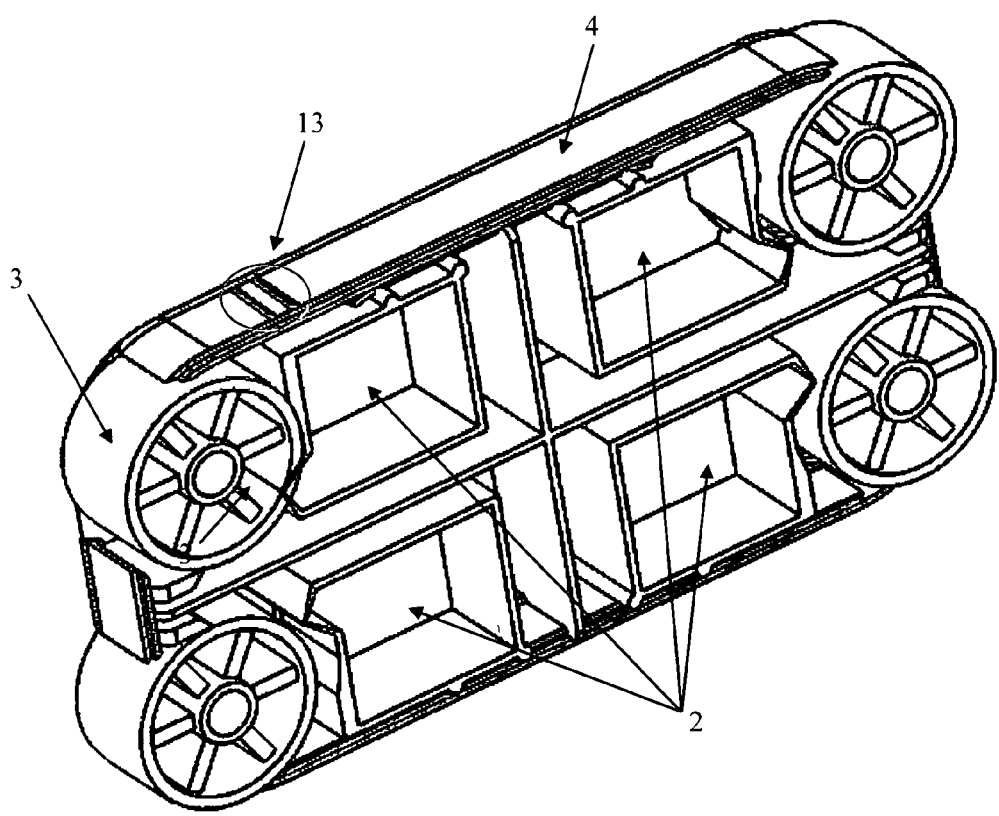
FIG. 6 shows a preferred embodiment of the invention, wherein the device comprises four detection mechanisms.

Referring to FIG. 6, an additional embodiment is described wherein the device (1) is provided with interconnecting means that allow the connection of two or more devices allowing the final commercial embodiment be a single-body multi-testing multi-component system.

Figure 7:
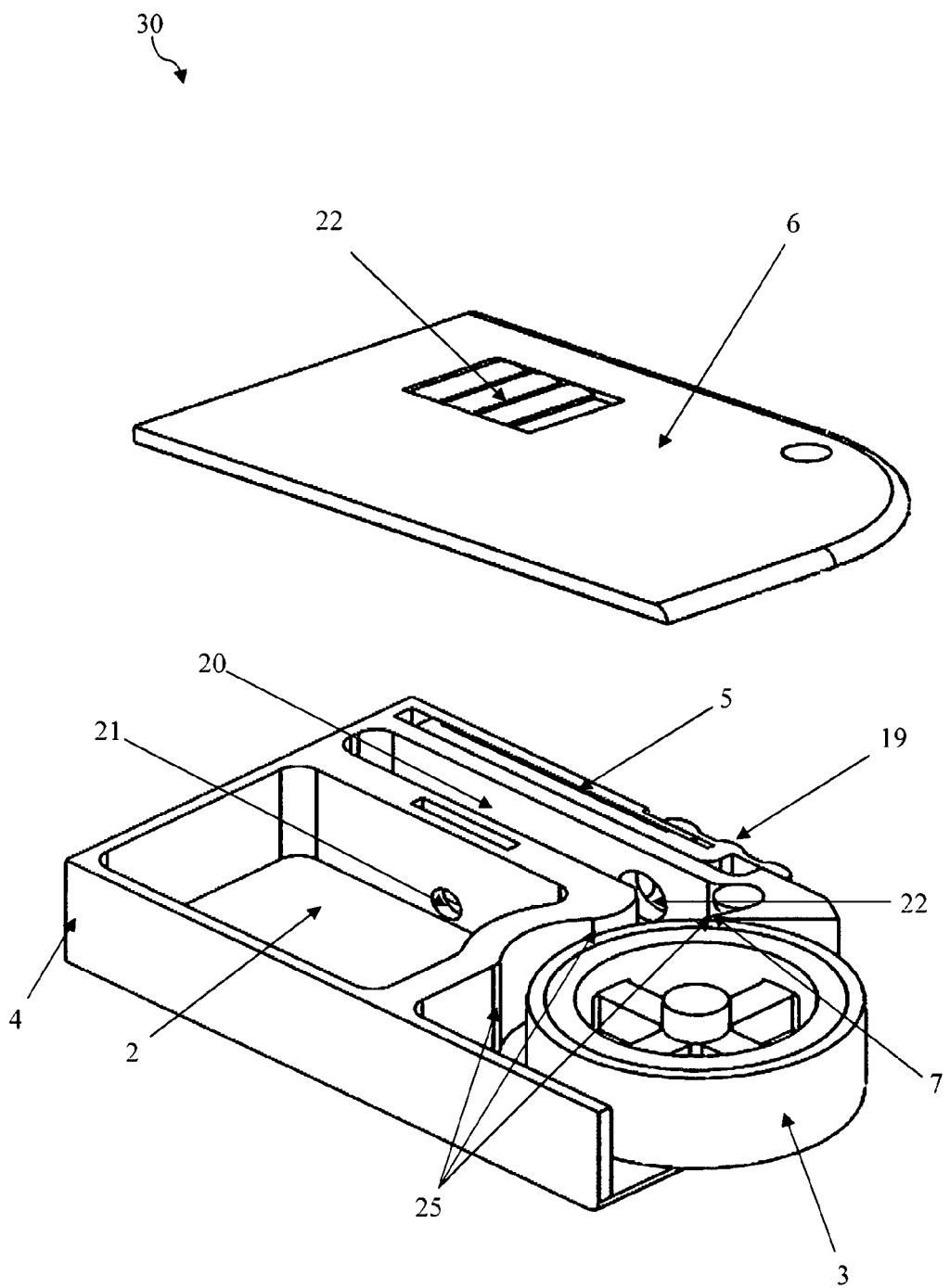
FIG. 7 is an isometric view of another preferred embodiment of the claimed device.

Referring now to FIG. 7, an additional preferred embodiment (30) is disclosed. This embodiment also comprises four distinguishing parts corresponding to: i) a collection and sealing system for sample collection; ii) a storage system containing the necessary fluid(s) for dilution or reaction of the sample; iii) a dilution chamber; and iv) a detection system.

Figure 8:
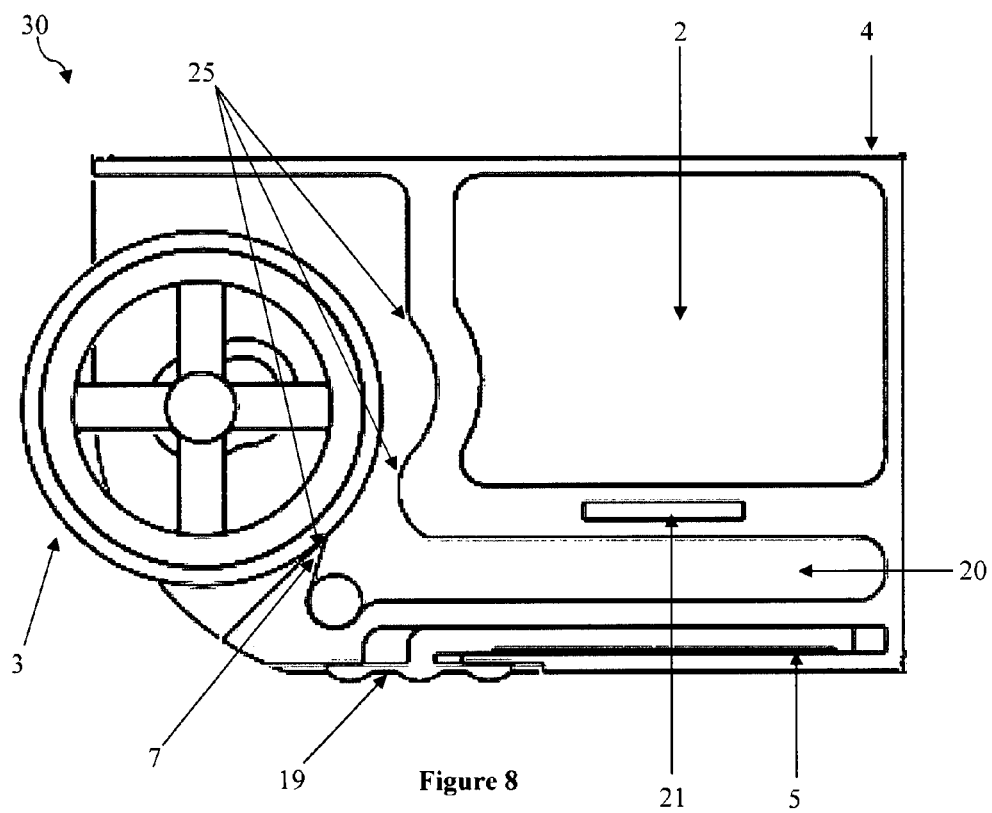
FIG. 8 shows a lateral internal view of the device in FIG. 7.

The embodiment (30) of FIGS. 7 and 8 includes the following elements:
   i) a storage tank (2);
   ii) a roll (3);
   iii) a cover base (4);
   iv) a membrane (5);
   v) three contact stops (25);
   vi) a cap (6);
   vii) an eyelash (22) that allows the entry of the dilution fluid into the dilution chamber (20);
   viii) a scraper (7);
   ix) an orifice (21) for the passage of the dilution fluid from the storage tank (2) to the dilution chamber (20);
   x) an orifice (22) for the passage of the diluted sample located in the diluting chamber (20) to the membrane (5); and
   xi) a sliding pin (19) that isolates the membrane (5) from the dilution in a first position, and in a second position places membrane (5) in contact with the diluted sample.

Referring to FIG. 8, scraper (7) is located next to the dilution chamber (20). This configuration provides more space to let diluting chamber (20) accumulate more sample to be analyzed.

Figure 9A:
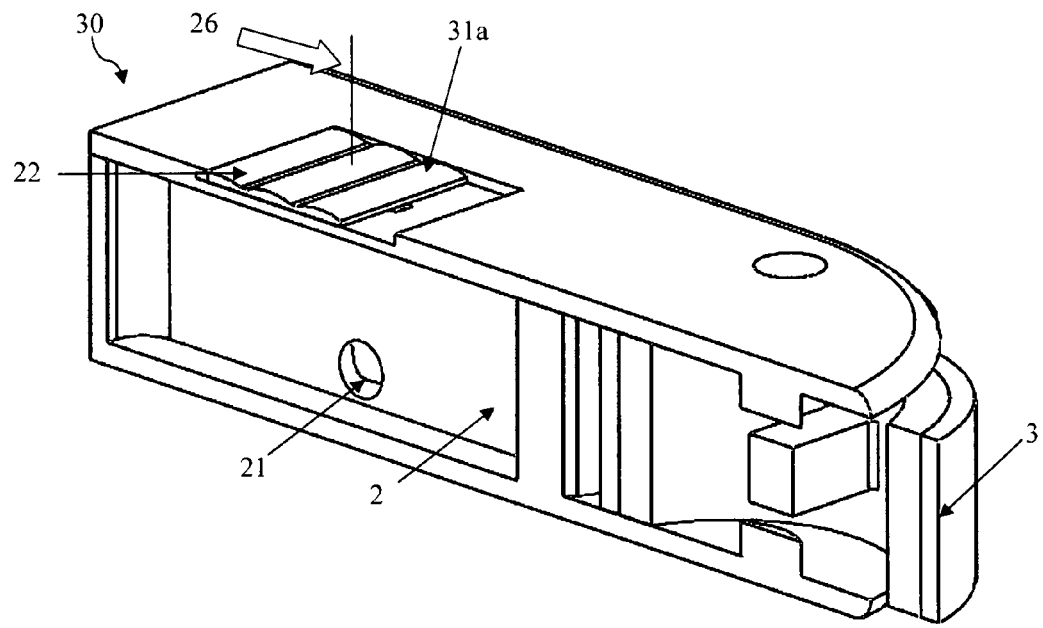
FIG. 9A is a section view of the device in FIG. 7 showing the closed position of the eyelash.
Figure 9B:
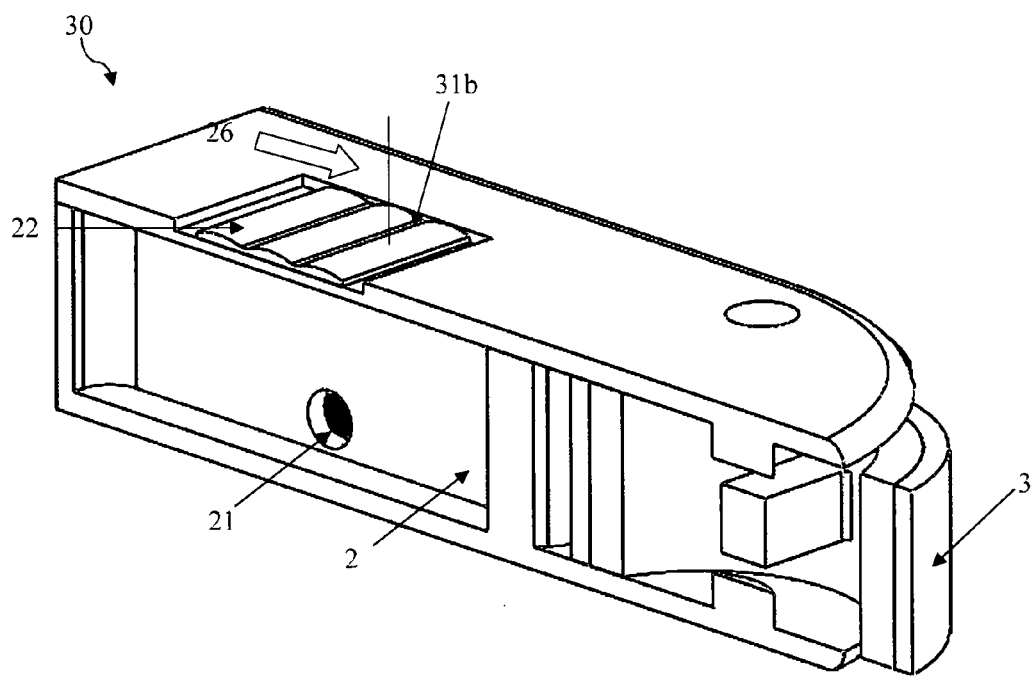
FIG. 9B is a section view of the device in FIG. 7 showing the open position of the eyelash.

Referring to FIGS. 9A and 9B, eyelash (22) is the element that allows the access of the dilution fluid located in storage tank (2) into the diluting chamber (20) when moved from an initial position (31a) to a second position (31b). Continuing with FIGS. 9A and 9B, eyelash (22) is in a closed position until collecting of the sample is completed. When force (26) is applied, eyelash (22) is moved by the operator from the closed position (31a) to the open position (31b) letting the dilution fluid flow into the dilution chamber (20) avoiding the breakage of the tank (2). Storage tank (2) is an independent structure that avoids any part breaking and also ensures that the dilution liquid will be totally verted into the diluting chamber (20) avoiding any liquid leakage.

Figure 10A:
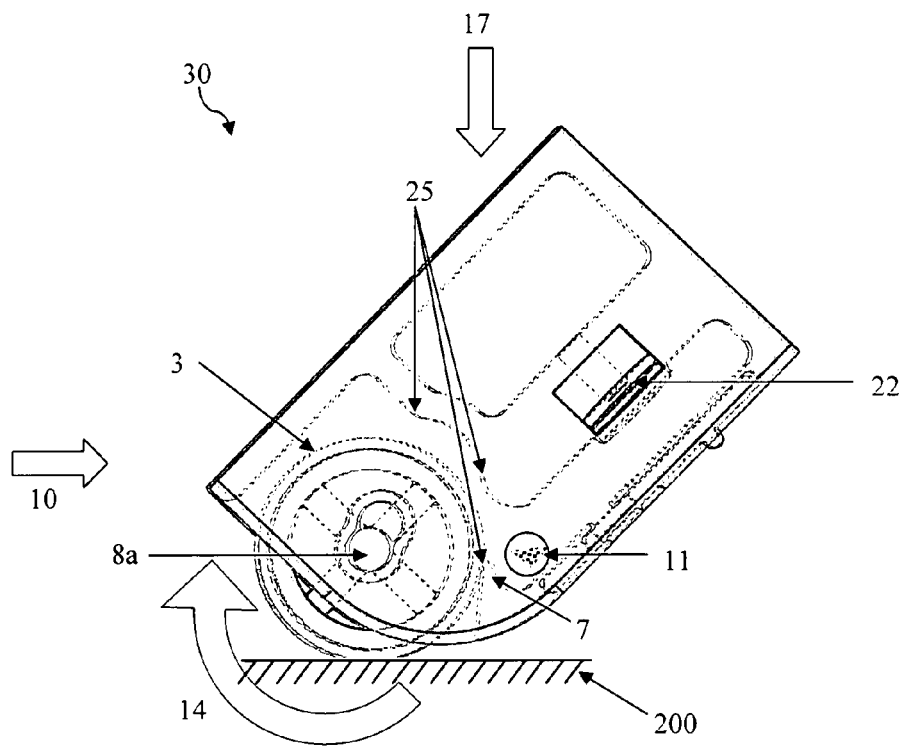
FIG. 10A shows the configuration of the device in FIG. 8 at the moment of collection.
Figure 10B:
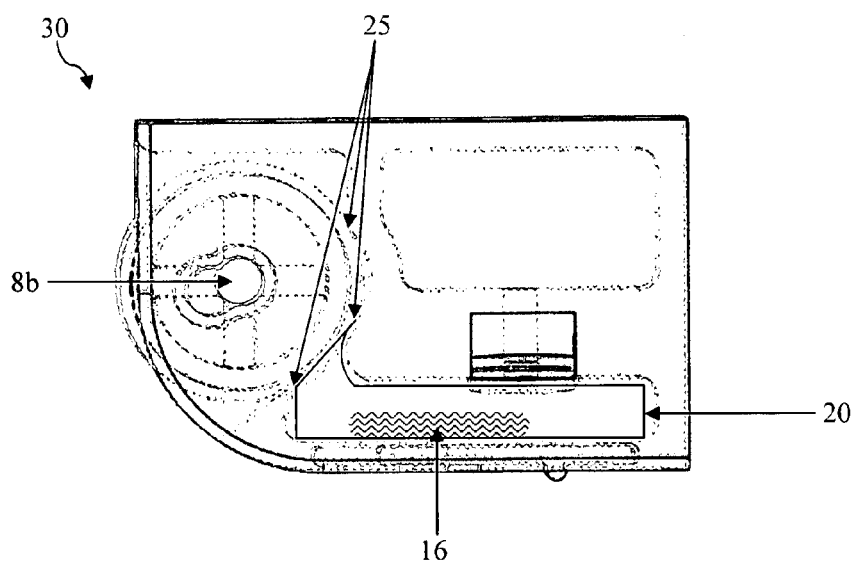
FIG. 10B shows the configuration of the device in FIG. 8 at the moment of reception of the sample.

Continuing with FIGS. 10A and 10B, cover base (4) comprises three contact stops (25) that guarantee that when roll (3) slides along track (8) from the initial position (8a) to the second position (8b), the sealing of the dilution chamber (20) by means of the roll's sheath pressure against the contact stops (25) of device (30). Here, the surface of roll (3) works as a hydraulic sealing system and as an element of adhesion such that the roll (3) permits the adhesion of the material collected. In preferred embodiments, the material of roll (3) is Ethyl Vinyl Acetate among other natural rubbers.

Figure 11A:
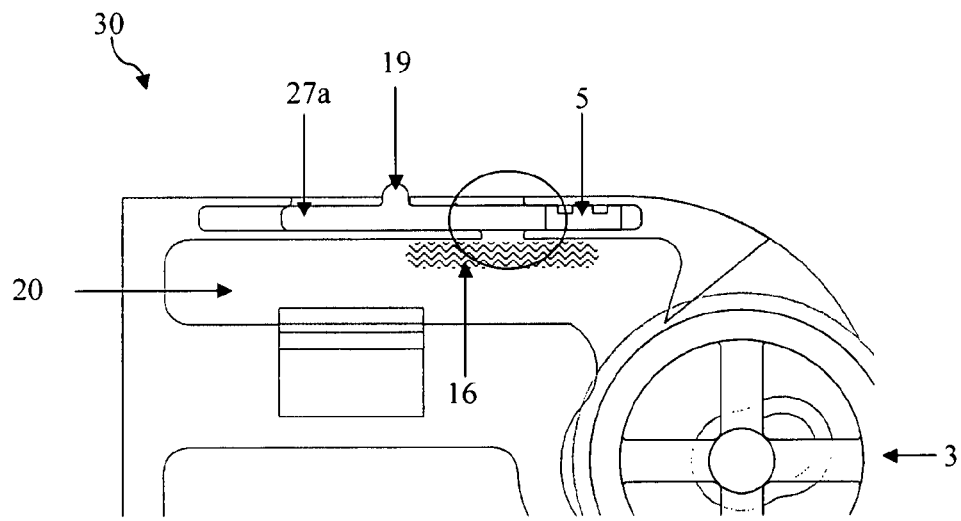
FIG. 11A shows a lateral view of the device in FIG. 8 with the movable pin in a closed position.
Figure 11B:
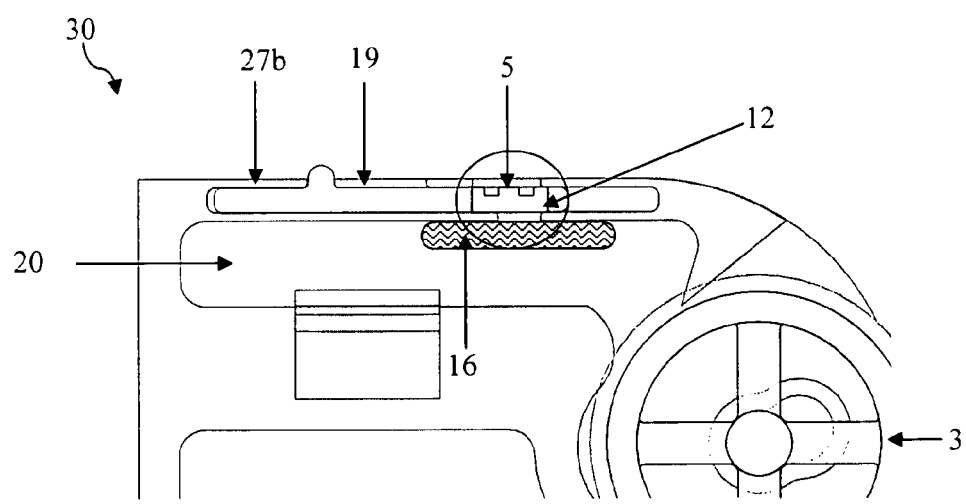
FIG. 11B shows a lateral view of the device in FIG. 8 with the movable pin in a open position.
Figure 12:
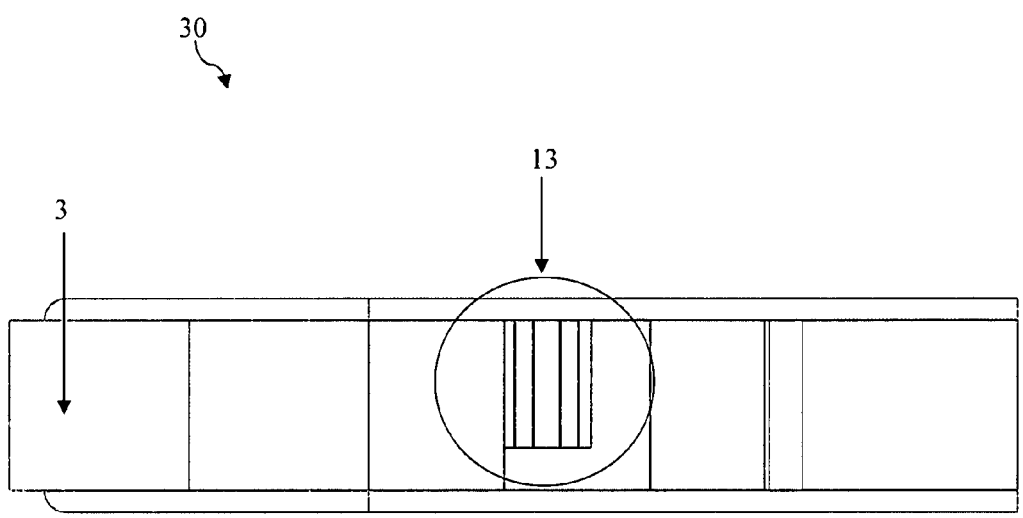
FIG. 12 shows an inferior view of the device of FIG. 8 displaying the result reading mechanism.

Referring to FIGS. 11A and 11B, there is disclosed a membrane (5) integrated into a sliding pin (19). After the dilution liquid is homogeneously mixed with the sample (11), membrane (5) can be moved from the first position (27a) to the second position (27b), exposing the membrane (5) to the dilution liquid (12). In preferred embodiments, a filter paper is located between the detection and sample reception zone

(20) and the membrane (5), in order to allow the passage of substances of interest and restrict the passage of substances that would affect the analysis.

The following is the method of use of the second embodiment (30):

Step 1: Sample Collection

The device of the second embodiment (30) follows the same procedure to collect sample (11) of the device (1). Roll (3), as shown in FIG. 10A, is placed on the surface (200) needing analysis and the roll is rotated by a forward motion (10). As the device (30) is moved forward, the roll (3) is rotated by a forward motion (10) and rolls in clockwise direction (14). Sample (11) is collected by roll (3) along its rough surface as it rolls and is removed by scraper (7). The forward motion (10) will continue in this fashion over the zone needing analysis until the required sample quantity is obtained in order to achieve detection. The sample collected (11) is stored between the scraper (7) and the device's wall as shown in FIG. 10A.

Step 2: Sample Preparation

After obtaining the needed amount for the corresponding sample (11), a force (17) is applied on the device (30) when it is still on the surface where the sample is collected. This displaces roll (3) along track (8) from the position (8a) to the position (8b). When this displacement occurs, the walls of the roll (3) and the device (30) seal the interior of dilution chamber (20).

Step 3: Dilution of the Sample

After dilution chamber (20) is isolated, eyelash (22) is pressed in direction (26), allowing the passage of the dilution liquid into dilution chamber (20). The second embodiment (30) ensures that the dilution liquid is almost totally verted into the dilution chamber (20), substantially avoiding any liquid leakage regardless of the inclination of the device. Afterwards, the equipment is shaken in order to achieve a homogenous solution inside.

Step 4: Sample Analysis

Referring to FIGS. 11A and 11B, after shaking the sample and homogenizing it, the sliding pin (19) that isolates the membrane (5) from the mixed liquid dilution (16) is slid from the first position (27a) to the second position (27b) letting the membrane (5) come into contact with the mixed solution (16). Once the mixed solution (16) is absorbed by the membrane (5), this reacts and shows the results in the output indicator (13) located in the bottom of the device (30).

Figure 13:
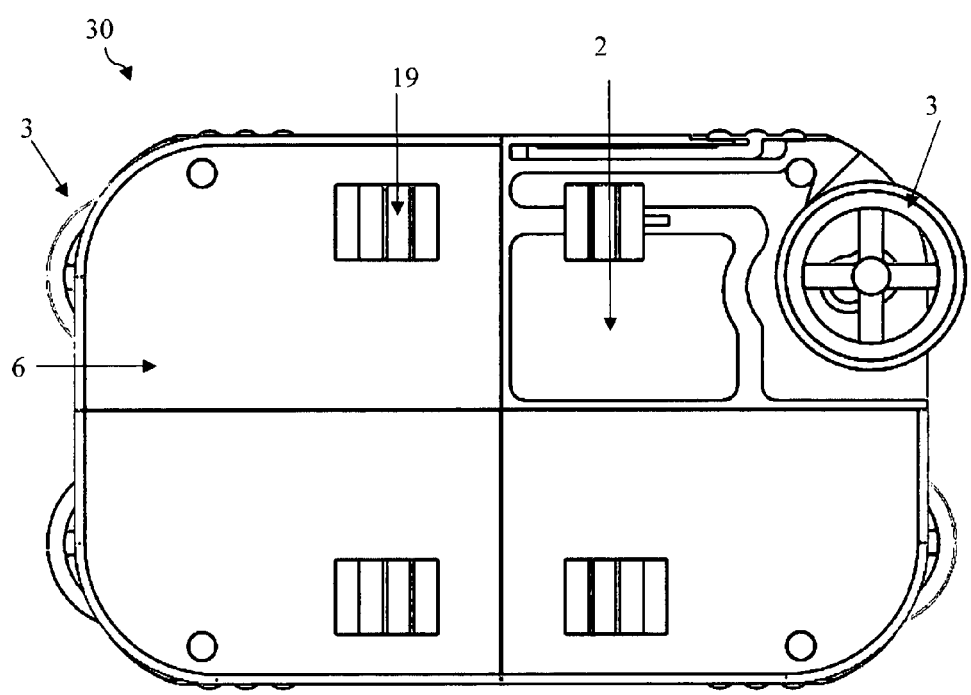
FIG. 13 shows another embodiment of the invention, wherein the device comprises four detection mechanisms.

The aforementioned embodiments are provided with interconnecting means that allow the connection of two or more devices allowing the final commercial embodiment be a single-body multi-testing device as shown in FIGS. 6 and 13. Additional embodiments may provide multiple storage tanks (2) within the cover base (4) in order to provide multiple dilution liquids for multiple reactions. Likewise, the construction of such embodiment requires an eyelash (22) capable of allowing the flood of diluting liquid into the diluting chamber (20).

The aforementioned constitutes a complete and detailed disclosure of different embodiments to practice the inventive concept herein claimed. Any skilled person in the art will understand that variations may be carried out without departing from the scope and spirit of the invention. The scope of the invention is defined by the following claims that shall be interpreted in accordance with what was disclosed herein.

The invention claimed is:

1. A substance sampling, dilution and detection device, comprising:
   a sample collection roller configured to transfer a sample from an exterior of the device to an interior of the device by rolling the sample collection roller, wherein the sample collection roller comprises a rotatable collection surface with a central axle;
   a dilution chamber operatively connected to the sample collection roller and disposed to receive the sample collected and a dilution liquid;
   a dilution liquid storage system operatively connected to the dilution chamber; and
   a detection system operatively connected to the dilution chamber and disposed to receive a mixture of the substance being sampled and the dilution liquid, in order to determine the presence of the substance being sampled;
   a scraper contacting the rotatable collection surface and configured to remove the sample from the sample collection roller while the sample collection roller rolls.

2. The device of claim 1, wherein the central axle of the rotatable collection surface is configured to shift along a track groove.

3. The device of claim 2, wherein the dilution liquid storage system comprises a weakened area, the weakened area facilitating breakage and spillage of the dilution liquid into the dilution chamber.

4. The device of claim 3, wherein the rotatable collection surface, upon shifting along the track groove, breaks the weakened area of the dilution liquid storage system.

5. The device of claim 2, wherein upon breakage of the dilution liquid storage system the rotatable collection surface seals the dilution chamber.

6. The device of claim 2, wherein the sample collection roller is configured to seal off the dilution chamber.

7. The device of claim 6, wherein the sample collection roller is configured to provide a seal between the sample collection roller and the dilution chamber that prevents the dilution liquid from exiting.

8. The device of claim 7, wherein the sample collection roller comprises a plurality of stops that come into contact with the rotatable collection surface when the central axle of the rotatable collection surface shifts along the track groove.

9. The device of claim 1, wherein the rotatable collection surface comprises an adherent.

10. The device of claim 1, wherein the dilution liquid storage system comprises one or more cavities for containing different types of solutions for dilution or reaction.

11. The device of claim 1, wherein the detection system comprises a membrane incorporating an element capable of detecting the presence of the substance being sampled by the device.

12. The device of claim 11, wherein, in a first position, a sliding pin isolates the membrane from the dilution chamber, and in a second position, places the membrane in contact with the mixture in the dilution chamber.

13. The device of claim 1, wherein the device is connectable to other similar devices so as to conform a multicomponent system.

14. A method to analyze and detect the presence of a substance in a single device, comprising:
   collecting a sample by contacting the sample with a roller that comprises a rotatable collection surface with a central axle;
   rolling the sample from the exterior of the device to a dilution chamber with a scraper contacting the roller surface and removing the sample from the roller while the sample is on the roller;
   mixing the sample with a dilution liquid inside the dilution chamber; and exposing the sample-dilution liquid mixture to a detection member configured to detect the presence of the substance being sampled.

15. The method of claim 14, wherein the single device is the device of claim 1.

16. The method of claim 14, wherein the detection member configured to detect the presence of the substance being sampled is a membrane containing an element capable of detecting the presence of the substance being sampled.

* * * * *